(12) United States Patent
Quittmann et al.

(10) Patent No.: US 8,114,996 B2
(45) Date of Patent: Feb. 14, 2012

(54) REDUCTION OF 5-(ARYL-DIAZENYL)-4,6-DIHALO-PYRIMIDINE

(75) Inventors: Wilhelm Quittmann, Visp (CH); Wei Zhu, Guangzhou (CN); Feng Ye, Guangzhou (CN); Rongmin Chen, Guangzhou (CN)

(73) Assignee: Lonza AG, Basel (CH)

( * ) Notice: Subject to any disclaimer, the term of this patent is extended or adjusted under 35 U.S.C. 154(b) by 184 days.

(21) Appl. No.: 12/160,343

(22) Filed: Sep. 28, 2010
(Under 37 CFR 1.47)

(65) Prior Publication Data
US 2011/0178298 A1 Jul. 21, 2011

(30) Foreign Application Priority Data

Feb. 13, 2006 (EP) .................................... 06002822
May 10, 2006 (EP) .................................... 06009627

(51) Int. Cl.
C07D 239/28 (2006.01)
(52) U.S. Cl. ..................................................... 544/316
(58) Field of Classification Search .................. 544/316
See application file for complete search history.

(56) References Cited

FOREIGN PATENT DOCUMENTS
WO WO2005/095358 * 10/2005

OTHER PUBLICATIONS

Beaman, Synthesis of 6-Fluoro-9-methylpurine, Nov. 27, 1962, Journal of Medicinal and Pharamceutical Chemistry, vol. 5, No. 6, p. 1067-1074.*

* cited by examiner

Primary Examiner — Andrew D Kosar
Assistant Examiner — Karen Cheng
(74) Attorney, Agent, or Firm — Hoffman & Baron, LLP

(57) ABSTRACT

Method of synthesizing a compound of formula (I), wherein R1, R2 are, independently, chloro or fluoro, and wherein R3 is H, alkyl, aralkyl or is an alkylether or alkylthioether comprising the steps of firstly reducing a diazeny compound of formula (II) non-catalytically or with a catalytic amount of an homogenous organic, non-metal catalyst to the corresponding hydrazo compound of formula (III) and in a second step catalytically hydrogenating said hydrazo compound in with a heterogeneous Ni-catalyst to the compound of formula (I).

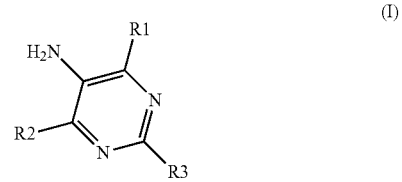

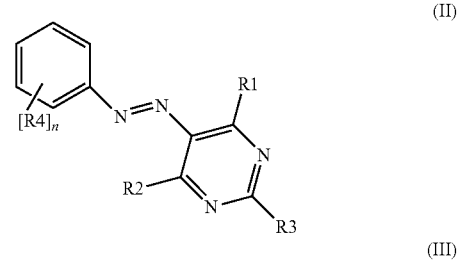

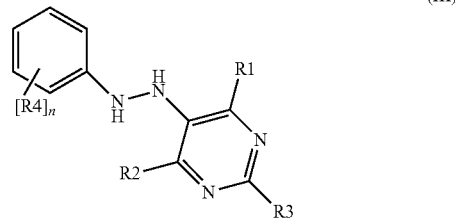

29 Claims, No Drawings

REDUCTION OF 5-(ARYL-DIAZENYL)-4,6-DIHALO-PYRIMIDINE

This application is the U.S. National Phase of, and Applicants claim priority from, International Application Number PCT/EP2007/001216 filed 13 Feb. 2007, European Application bearing Serial No. 06002822.2 filed 13 Feb. 2006 and European Application bearing Serial No. 06009627.8 filed 10 May 2006, which are incorporated herein by reference.

BACKGROUND OF THE INVENTION

The present invention relates to the field of catalytic hydrogenation. It devises a method for hydrogenating aryl-azo-pyrimidines to yield the corresponding amino-pyrimidine.

Furst et al., (1957) J. Am. Soc. 79:5492, described successful and convenient reduction of bisaryl-azo compounds to the corresponding hydrazo compounds by hydrazine in the presence of Raney Ni. However, further reductive cleavage to the primary, aromatic amine was found difficult to achieve, being strongly biased by electronic substituent effects and further subject to the irritating and inconvenient observation of requiring particularly dilute reaction mixture. The latter may be accounted for by the fact that Furst's reaction conditions proved not be a transfer hydrogenation reaction but that the metal catalyst only generated the directly reducing reagent, diimide, in situ from the hydrazine by way of a disproportionation reaction as evidenced by the generation of considerable amounts of ammonia during the reaction (Ioffe et al., 1969 J. Org. Chem. USSR 5,1683). The catalyst did not allow of hydrid transfer here.

WO 05/095358 describes a one pot process to catalytically reduce 4,6-dichloro-5-(4-methylphenyl)diazenyl-2-(propylsulfenyl)pyrimidine to 4,6-dichloro-2-(propylthio)-pyrimidin-5-amine. The reaction was carried out in a hydrogenation vessel at 3 bar hydrogen pressure with a biphasic temperature profile, initially allowing of the reduction to the corresponding hydrazo compound at lower temperature and converting the latter to the amine at higher hydrogenation temperature only. The yield obtained was about 80%, apparently improving over the WO 01/92263 from same applicant on the same reaction by virtue of temperature regime. In both patent applications, only the use of noble metal catalysts such as Pt, Pt/V or Pd catalysts is taught.

As a disadvantage, only noble metal catalysts such as Pd or preferably Pt were used, at unusually high catalyst loadings of 10% (w/w). At an industrial scaled process, nobel metal catalysts usually necessitate tiresome recovery and recycling of the catalyst when working up the reaction broth; this is required for sustainable process, since the noble metal raw metals are getting an ever more scarce source. Already, in some areas of technology, supply of some rare metals is already facing exhaustion and hence unavailability of metal itself. Such development has also been forecasted for Pt and Pd. Further, Pd and Pt are particularly liable to poisoning by thioesters and thiols, resulting in increased loading rates. Finally, given the expensive nature of metal catalysts, the yield of the Pt/C catalyzed process await further improvement.

It is the object of the present invention to devise another method of conducting the reducting of said and closely similar 5-diazenyl-pyrimidine to the corresponding 5-amino-pyrimdine.

DESCRIPTION OF THE INVENTION

This object is solved by the method of synthesizing a compound of formula I,

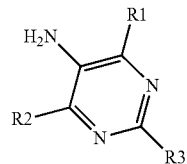

Wherein R1, R2 are, independently, chloro or fluoro, and wherein R3 is H, aralkyl, alkyl, an O-alkylether (meaning alkoxy) or S-alkylthioether, the alkyl moiety being linear or branched and preferably being C1-C10, more preferably being C1-C4, Comprising the steps of firstly reducing a diazenyl compound of formula II

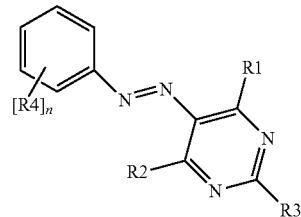

Wherein R1, R2, R3 are defined as above, n=0 to 5 and wherein each R4$_n$, independently, is halogeno, preferably is chloro or fluoro, or is alkyl or alkoxy, preferably is C1-C6 alkyl or alkoxy, non-catalytically or with a catalytic amount of an homogenous organic, and preferably non-metalorganic, non-catalytically or with suitable catalytic amounts of an organic, homogenous catalyst, preferably an organic and homogenous non-metal catalyst, to the corresponding hydrazo compound of formula III

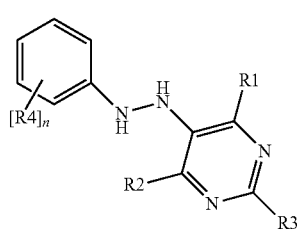

and in a second step catalytically hydrogenating said hydrazo compound III with a heterogeneous Ni-catalyst to the compound of formula I.

Suitable Ni-catalysts are known in the art, for example, Raney-Ni or Ni boride (NaBH$_4$ reduced Nickel, cp. Nakao, Chem. Lett. 997, 1982). Preferably, the catalyst is Raney-Ni as commonly known in the art: Raney-Ni is prepared by alkaline attack on aluminium rich Al/Ni alloys, extracting selectively the Al. The base extraction leaves behind a sponge-like, Ni crystallite having a high specific surface of typically at least 50 m$^2$/g up to 150-300 m$^2$/g; due to the mode of preparation, typically such Raney-Ni catalyst comprises some variable residual amount of Al (also in the form of oxide), typically of less than 10-20% Al by weight. Examples of Raney-type catalysts, their composition and preparation may be found in U.S. Pat. No. 5,554,573. Preferably, a Raney Ni catalyst according to the present invention is a powder; some commercially available Raney Ni catalyst available as spherical granulates may work less well.—In the context of the present invention, a catalytic hydrogenation, in the context of the present invention, is not confined to H2 (g) borne hydrogenation but also comprises commonly known transfer hydrogenation systems using a heterogeneous metal catalyst and a hydride donor, such as ammonium formate, cyclohexene or metal hydrides such as $CaH_2$, for instance. Preferably, the catalytic heterogenous hydrogenation is carried out with gaseous hydrogen as the hydride donor.

Surprisingly and contrary to initial expectations, it has been found that in principle less active Ni hydrogenation catalysts such as Raney Ni allow of obtaining better product yields than the prior art methods, despite a concomittant need for harsher reaction conditions when using Ni catalyst: Higher hydrogen pressure and much longer reaction times (of from 5 to 20 hours) for the hydrogenation reaction needed to be applied. Still then the result obtained with the Ni catalyst was superior compared to the Pt-catalysts of the prior art. A catalyst in the understanding of the present invention is not substantially consumed by the reaction and merely serves to accelerate reaction rate is used in substoichiometric amounts, that is it is used in amount less than 0.5 eq., preferably used in amount less than 0.2 eq., more preferably used in amount less than 0.05 eq. of educt or starting material.

More surprisingly, the superior result of the method of the present invention was unexpectedly found to be dependent on conducting the first reduction of the diazenyl compound II to the corresponding dihydrazo compound III non-catalytically, that is without using a heterogeneous Ni metal catalyst, and more preferably also without using a metal-organic, homogenous catalyst.—When using a Ni catalyst for straightfoward reduction of the azo compound similar to the prior art approach, the spectrum of side products increases drastically, the most dominant single side reaction being reductive dehalogenation of the pyrimdine core. No satisfactory compromise could be found in between dissatisfactory conversion rate/reaction time and the amount of impurities formed during reaction. Unexpectedly and according to the present invention, the problem of sideproducts formed may be avoided if starting from the hydrazo compound II for catalytic hydrogenation only.

A variety of the commonly known chemical reducing agents may be used for the first, non-catalytic reduction step for converting the diazenyl compound of formula II to the hydrazo compound of formula III. Metal or mixed metal hydrides such $LiAlH_4$ may be feasible for obtention of the hydrazo compound III only if used in very large excess and under extreme reaction conditions as has been reported for azobenzene (Ioffe et al. supra), but are strongly dispreferred for working the first reduction step. More suitable, commonly known reducing agents are diimide HN=NH (Ioffe et al., supra), Ni-salt promoted reduction by metallic Li in the presence of catalytic amounts of an arene (Alonso et al., Fourth International Electronic Conference on Synthetic Organic Chemistry (ECSOC-4), www.mdpi.org/ecsoc-4.htm, Sep. 1-30, 2000, Abstract 0020; cp. http://pages.unibas.ch/mdpi/ecsoc-4/a0020/a0020.htm), reduction with dithionite, formate, Zn/H+ or suitable redox couples as for instance Zn with Cu salt ('activated Zn'), Cu characteristically used in quantitative, stoichiometric or overstoichiometric amounts as to yield a corresponding alloy, or Zn-ammonium formate couple in suitable stoichiometric amount, for example. It may also be possible to use further multiple combinations of such redox couples such as Zn—Cu with ammonium formate. Further, the present inventors do not want to be bound by theory by the using the term 'couple' whether formate in combination with Zn is necessarily at least partly serving as a reducing agent or is as, as a mere ionic ligand, simply well-suited in complexing Zn/Zn2+ and finetuning the reduction potential of metallic as to allow neatly and quantitatively of reduction of the azo compound II to the hydrazo compound III. Preferably, Zn is used in 1-1.5 eq. per 1 eq. of diazenyl educt of formula II. As is evidenced in the experimental section, amounts of at least 2 eq. of Zn/H+, e.g. Zn/HOAc, lead to straightforward and undesirable reduction of diazenyl compound II directly to primary amine concomittant with excessive dehalogenation. Interestingly, this undesirable outcome outside the scope of the present invention could not not be influenced by using less acidic proton donors such as ammonium salts, ammonium formate in particular, or a hydrogencarbonate salt such as an alkali hydrogencarbonate, for instance. Stoichiometric control is decisive when using reducing agents and in particular Zn for the first reduction step according to the present invention.

When using Zn or e.g. Zn—Cu couple, in a less preferred though feasible embodiment, in combination with formic, acetic or other carboxylic acid as a reducing agent, the acid component may better be dosed to the reaction, for controlling redox potential. Further, since the hydrazo compound III newly formed is not very stable in acidic condition, not only any unreacted Zn but excess acid should be removed/neutralized prior to catalytic hydrogenation with Ni. The hydrazo product III formed may subject to benzidine type rearrangement even under mildly acidic condition. At mildly acidic pH, the cinetics of such reaction is mononuclear, at more strongly acidic condition, it is proceeding at second order rate. Hence when using acidic condition for obtaining the hydrazo compound III, the reaction time should be minimized and the pH readjusted to at least neutral or basic pH as quickly as possible after the first reduction step according to the present invention. Palladized Zn or palladized Zn—Cu couple are not understood as to amount to non-catalytically active reducing agents in the present context, in contrast.

Diimide is readily producible for the first reduction step in situ from hydrazine; Cu (Ioffe et al, supra), Ni catalyst such as Raney-Ni (Furst et al., (1957), J. Am. Chem. Soc. 79:5492) or the alloy-like borides of Co, Ni, Rh such as e.g. Co boride (Pratt et al., Cobalt Boride as a heterogenous catalyst, J. of the Chemical Society D: Chemical Communications (1969) 22:1231-1322 may be used for such. Since not involved directly in the reduction of the azo compound II according to the present invention, the use of hydrazine and an imide-generating catalyst is not deemed a 'catalytic' but a non-catalytic reduction within the context of the present invention. Optionally, no hydrazine is used for the first reduction step according to the present invention.

Preferably, the reducing agent for the first reduction step comprises dithionite, Zn or diimide, the latter preferably generated in situ. An even more strongly preferred embodiment for the first reduction step is using $Na_2S_2O_4/NaHCO_3$ and/or $Zn/HCOONH_4$ (Gowda et al., Reductive cleavage of azo compounds catalyzed by commercial zinc dust using ammonium formate, Tetrahedron Letters 43, 2002, 1329-1331) as a reducing agent, allowing in the context of the present invention to neatly limit the reaction to the first reduction step of furnishing the hydrazo compound of formula III and V, respectively. Such first reaction can be carried out conveniently at room temperature according to such embodiment.

Preferably, the amount of noble metal catalyst loading in the catalytic hydrogenation is of from 0.1 to 100% (weight of catalyst/weight of hydrazoeduct of formula III), more preferably of from 1 to 40%, most preferably of from 5 to 20%.

Preferably, the hydrogenation is carried out in the presence of a polar solvent or solvent mixture preferably comprising a water-miscible alcohol such as methanol, ethanol, n-propanol or isopropanol or mixtures thereof or mixtures thereof with at least one amphilic solvent preferably selected from the list consisting of aceton, acetonitril or tetrahydrofuran, more preferably with aceton, most preferably in a mixing ratio of 0.5 to 1.5 parts of any of said three solvents with said water-miscible alcohol. Preferably, said water-miscible alcohol or their/its mixture with said at least one amphilic solvent amounts to at least 80%, more preferably at least 90%, most preferably at least 95% of the solvent volume.—The same solvent system preferably is used for the first, non-catalytic reduction step.

The catalytic hydrogenation may be carried out at 0 to 120° C., preferably it is carried out at 15 to 60° C., most preferably at 20° C. to 50° C., and very most preferably at 20° C. to 40° C. A hydrogenation temperature of about 30° C. may be optimal in view of yield; notably, above about 60° C., some slow decomposition of the desired product of formula I may occur, asking for a trade of reaction temperature vs. reaction time for the hydrogenation step. Further preferably the catalytic hydrogenation is carried out at a hydrogen pressure of from 0.5 to 100 bar, preferably of from 2 to 20 bar, more preferably at 5 to 15 bar, most preferably of from 8 to 12 bar (0.8 to 1.2 Mpa) hydrogen pressure. The reaction time for catalytic hydrogenation may usually be in the range of 1 to 50 hours, more preferably is 5 to 40 hours, most preferably is 6 to 15 hours. Extending the reaction time unnecessarily beyond the moment of maximum yield tends to slightly decrease total yield; for optimal conversion, violent stirring is required during hydrogenation. Sufficient stirring or mixing is discernible by achieving near constant conversion rate throughout the reaction.

It is strongly preferred that the Ni catalyst is Raney-Ni, alone or in combination with the other preferred embodiments mentioned herein. Raney-Ni is widely applied in industrial analysis and well known; descriptions may be found e.g. in Birkenstock U, Holm R, Reinfandt B and Storp S. J. Catal., 1985; 93: 55-67; Raney, M., U.S. Pat. No. 1,563, 787. It is further possible and preferred according to the present invention that Raney-Ni, as a large-surface solid metal catalyst material, comprises similar to the redox couples mentioned above trace amounts of other metal such as e.g. Mo, also commonly referred to as promoters in the art. The alloy used for constituting the Raney-Ni catalyst is deliberately dotated with such metals. Preferably, such promoter metal is selected from the list consisting of Mo, Fe, Cr or V, or combinations thereof. Most preferably the promoter element is Mo. Examples of such may be found in EP-647472 A.

Preferably, such promoter is comprised by the Raney Ni catalyst in an amount of 0.01 to 20% by weight, more preferably the Raney-Ni catalyst comprises less than 10% by weight of such promoter metal, most preferably it comprises less than 5% of such promoter metal according to the present invention.

Examples of working embodiments for the present invention, though not being limited thereto, are given in the experimental section.

The educts and intermediate products according to the present invention are further objects of the present invention and are claimed as such.

According to the present invention, a further object is a compound of formula II

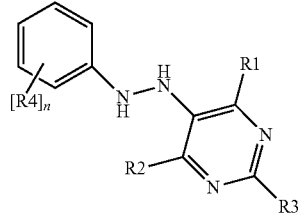

or of formula III

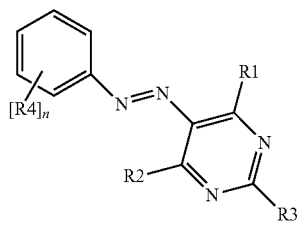

wherein R1, R2 are, independently, chloro or fluoro, and wherein R3 is H, aralkyl, alkyl or is an alkylether or alkylthioether, the alkyl moiety being linear or branched and preferably being C1-C10 alkyl, more preferably being C1-C4 alkyl, and wherein n=1 to 5 and wherein each R4$_n$, independently, is halogeno or is alkyl or is alkoxy, preferably wherein halogeno is chloro or fluoro and preferably wherein alkyl is C1-C6 alkyl or alkoxy, with the proviso, that at least one R4$_n$ is halogeno and/or with the proviso that where R3 is a C1-C4 alkylthioether radical, preferably where R3 is S-propylthioether radical, then either is n>2 or R4$_n$≠p-alkyl, preferably is R4$_n$≠p-methyl, and/or with the proviso, that where R3 is C1-C6 alkyl, preferably that where R3 is methyl, in formula II and only in formula II (and hence is mandating only a corresponding disclaimed radical for a structure of formula II but not of formula III), more preferably that where R3 is C1-C6 alkyl or is methyl in formula I or II (and hence is mandating a corresponding disclaimer for radical R4 both in the structure of formula II and/or formula III), that then either is n>2 or R4≠p-chloro or o-chloro preferably wherein n=1, in formula II only or in formula I and/or II respectively, more preferably that then R4≠chloro preferably wherein n=1, most preferably that then R4≠o-halogeno, p-halogeno, p,o-dihalogeno or o,o-dihalogeno wherein n=1 or 2 in formula II only or in formula I and/or II respectively.

EXAMPLES

1. Comparative Example I

Reduction of 5-(phenyl-diazenyl)-4,6-dichloro-2-(n-propylsulfenyl)-pyrimidine with Pt/C

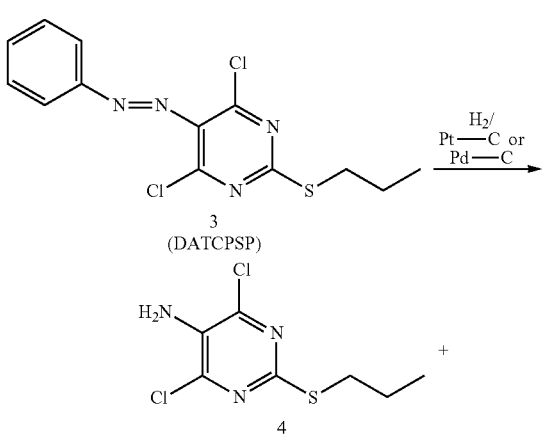

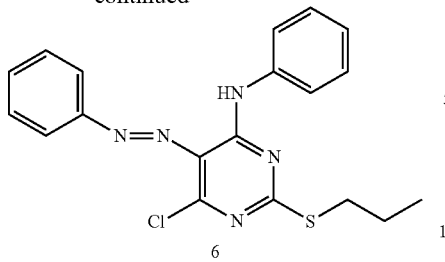

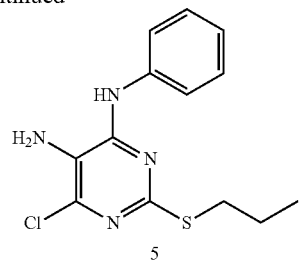

A stirred solution of 5-(phenyl-diazenyl)-4,6-dichloro-2-(n-propylsulfenyl)-pyrimidine (10.0 g, 0.30 mol, 1.0 eq) in methanol (50 mL) and i-propanol (50 mL) was hydrogenated for 32 hours at R.T/0.6 MPa over Pt—C (0.51 g, 5% w/w Pt/C), after nitrogen flushing of the autoclave hydrogenation vessel. The hydrogen gas pressure was released and the mixture was filtered and washed with 10 mL methanol. After removal of the solvent, the mixture is dissolved in 50 mL ethylacetate ester (EA) and washed with aequeous 0.1% HCl. The water phase was extracted by 10 mL EA. The combined EA phase was concentrated, to give 6.7 g crude product. The crude product was mixed with n-hexane (38.8 mL). After stirring for 5 mins, the black oil was separated by centrifugation. Carbon powder (0.41 g) was added to absorb the colorant. After concentration under vacuum, 3.1 g of compound 4 were obtained as reddish oil, yield: 40%; purity: 90% as identified by HPLC and LC-MS.

The reductive dehalogenation of the educt 3 and coupling with the initial aniline byproduct generated concomittant with 4 to give the byproduct 6, was found to be a dominant side reaction (10-20%), accounting along with lots of other unknown impurities for the low yield of the desired product 4. Adding an acidic agent such as citric or acetic acid to the hydrogenation, expected to protonate and hence neutralize further reactivity of the aniline did not work in improving yield of 4 in any way. Undesired competition of multiple reaction paths and diverging chemoselectivity of different reducing agent upon reduction of halo-compounds has in principle been reported similarly in the literature, e.g. when reducing halo-compounds to olefins (cp. Gero et al., J. Org. Chem. 16, 1731-1735 (1951)).

Interestingly, in repetition experiments using Pt—C, lowering of the hydrogen pressure only helped extending reaction time but did not substantially affect yields obtained either way, lowering the amount of catalyst used in the reaction strongly reduced the yield of compound 4 irrespective of hydrogen pressure applied.

2. Comparative Example II

Reduction of 5-(phenyl-diazenyl)-4,6-dichloro-2-(n-propylsulfenyl)-pyrimidine with Zn/HOAc

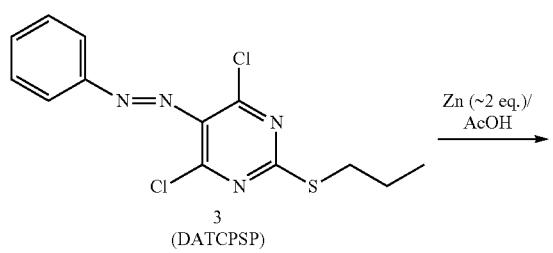

5-(phenyl-diazenyl)-4,6-dichloro-2-(n-propylsulfenyl)-pyrimidine (6.0 g, 0.018 mol, 1.0 eq.) was dissolved in methanol (40 mL) and 10 ml 40% acetic acid. Zinc powder (82% pure, 4.0 g, 0.050 mol, 2.6 eq.) was added in sequence. Reaction completed in 5-10 mins and the reaction mixture was filtered through a celite pad. Analysis of the reaction mixture by LC-MS showed one dominant product only had been mainly formed, which exceeded the molecular mass of the expected product 4 and supposedly was compound 5 resulting again from dehalogenation of the pyrimidine core.

Substituting the acetic acid with at least 2 eq. of ammonium formiate did not change the outcome of the reaction.

3. Synthesis of 5-(phenyl-diazenyl)-4,6-dichloro-2-(n-propylsulfenyl)-pyrimidine Step a.: Diazotisation: 98% $H_2SO_4$ (41.7 g, 0.426 mol, 1.0 eq.) was diluted in water (513 mL). After cooling to 0° C., aniline (39.3 g, 0.422 mol, 1.05 eq.) was added, followed by adding $NaNO_2$ (30.6 g, 0.443 mol, 1.1 eq.) solution in water (50 mL). The mixture was kept at this temp. for 30 mins. In parallel, 2-thiopropyl barbituric acid (75.0 g, 0.403 mol, 1.0 eq.) was diluted in a solution of NaOH (16.9 g, 0.423 mol, 1.05 eq.) in 162 mL water. The latter solution was dosed to the former. After agitating for 45 min at 0° C., the mixture was filtered. The cake was washed with water until sulfate free. The wet cake was vacuum dried at 60° C. 102.3 g of 5-(phenyl-diazenyl)-4,6-dihydroxy-2-(n-propylsulfenyl)-pyrimidine product were obtained, yield: 88%; purity: 95%.

Step b: Chlorination: Pyridine (12.5 g, 1.8 eq.) was added into a stirred, heated (70° C.) slurry of the product from step a (25 g, 0.086 mol, 1.0 eq) in methylcyclohexane (75 mL). $POCl_3$ (92 g, 7.0 eq.) was added dropwise in 30 mins. After heated for 5.5 h at 90° C., 40 g solvent was removed under vacuum. Then 100 mL cyclohexane was added after cooled to R.T., washed by ice-cold water (100 mL), saturated $NaHCO_3$ (100 mL) and water (100 mL). The organic phase passed a very short silica gel pad. After removing the solvent, got 22.3 g of product 3, yield: 80%; purity: 98%.

4. Reduction of 5-(phenyl-diazenyl)-4,6-dichloro-2-(n-propylsulfenyl)-pyrimidine to 5-amino-4,6-dichloro-2-(n-propylsulfenyl)-pyrimidine 5-(phenyl-diazenyl)-4,6-dichloro-2-(n-propylsulfenyl)-pyrimidine (6.1 g, 0.019 mol, 1.0 eq.) was dissolved in methanol (48.8 mL) and i-propanol (12.2 mL). Zinc powder (82% pure, 2.0 g, 0.025 mol, 1.3 eq.) and ammonium formate (3.8 g, 0.060 mol, 3.2 eq.) were added in sequence. Reaction completed in 10 mins, the mixture was filtered under $N_2$ protection. The filtrate was hydrogenated for 11 hours at RT/1.0 MPa over Raney Ni (0.62 g wet weight, 10% loading, 0.5% Mo/Degussa BKX111 W activated Ni catalyst, Degussa product code #48.5198.0000.00). Then the pressure was released, part of solvents was removed under reduced pressure at 35° C. The remained 23 g reaction mixture was acidified by 61 mL 10% HCl, extracted by n-hexane (30*3 mL). The combined organic phase was stirred at R.T for 20 mins with silica gel (1.0 g). After filtration and removal of the solvent, got 3.91 g 5-amino-4,6-dichloro-2-(n-propylsulfenyl)-pyrimidine, purity: 97%, yield 88%.

TABLE I

Reaction sequence of examples 3. and 4.

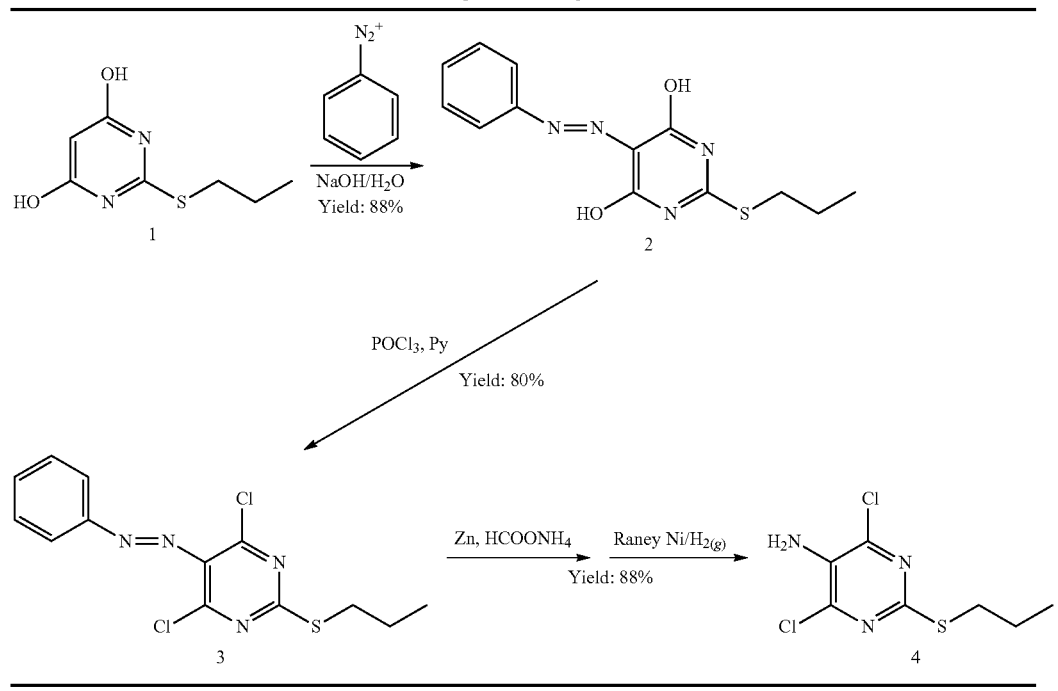

5. Reduction of 5-(phenyl-diazenyl)-4,6-dichloro-2-(n-propylsulfenyl)-pyrimidine to 5-amino-4,6-dichloro-2-(n-propylsulfenyl)-pyrimidine a. Preparation of Raney-Ni
Ni catalyst was freshly prepared in lab by the following procedure: 128 g NaOH pellets were dissolved in 500 ml bidest. water. 100 g Ni—Al Alloy (50% Ni w/w) was added in small portions to the 50° C. NaOH solution. The mixture was kept at 50° C. After the entire alloy was added, the suspension was digested at 50° C. for 50 mins with gentle stirring. Then the suspension was cooled at 0° C., washed by 500 ml pure water, 250 ml ethanol twice. The Raney Ni was stored in i-propanol, total volume being 205 ml (=Raney Ni at 0.24 g/ml).
b. Chemical Reduction and Hydrogenation Step
5-(phenyl-diazenyl)-4,6-dichloro-2-(n-propylsulfenyl)-pyrimidine (6.1 g, 0.019 mol, 1.0 eq.) was dissolved in methanol (43.9 mL) and i-propanol (12.2 mL) under forced stirring, eventually in a water bath set at 30 to 40° C. for helping dissolving solid, dried material; a share of finely dispersed material was accepted. Zinc powder (2.0 g, 0.025 mol, 1.3 eq.) and ammonium formate (3.8 g, 0.060 mol, 3.2 eq.) were added in sequence. The reaction completed in 10 min. as indicated by fading of the initially red-coloured reaction broth, whereafter the reaction mixture was filtered over Celite under nitrogen atmosphere. The filtrate was hydrogenated for 11 hours at 28° C./1.0 Mpa over Raney Ni (0.62 g wet weight, 10% loading). Then the pressure was released, part of solvents was removed under reduced pressure at 35° C. The remainder of 23 g reaction mixture was acidified by 61 mL 3% HCl and were extracted by n-hexane (2×45 mL). The combined organic phases stayed at RT for 2 h until completely transparent. After filtration, the product was recovered by solvent evaporation. The yield amounted to 78%, with approx. 98% purity.

6. Reduction of 5-(phenyl-diazenyl)-4,6-dichloro-2-(n-propylsulfenyl)-pyrimidine to 5-amino-4,6-dichloro-2-(n-propylsulfenyl)-pyrimidine Essentially, the reaction was carried out as described in section 5.b above, except that the Raney Ni catalyst employed this time was a fine powdered Raney Ni comprising 1.2% Mo (Degussa Raney-Ni, BK111 W 1.2%). Endpoint of reaction was determined by monitoring hydrogen consumption rate. The yield obtained was 94% (with 97% purity).

The invention claimed is:
1. A method of synthesizing a compound of formula I,

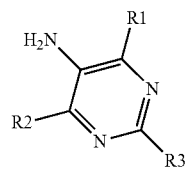

I wherein R1, R2 are, independently, chloro or fluoro, and wherein R3 is H, alkyl, aralkyl or is an alkylether or alkylthioether, the alkyl moiety being linear or branched, comprising the steps of firstly reducing a diazenyl compound of formula II

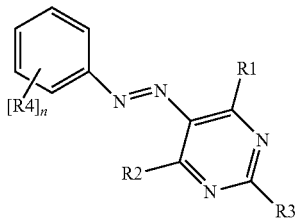

wherein R1, R2, R3 are defined as above, n=0 to 5 and wherein each $R4_n$, independently, is halogeno or is alkyl or alkoxy, non-catalytically or with a catalytic amount of an homogenous organic, non-metal catalyst to the corresponding hydrazo compound of formula III

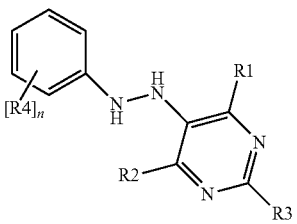

and in a second step catalytically hydrogenating said hydrazo compound III with a heterogeneous Ni-catalyst to the compound of formula I.

2. The method according to claim 1, characterised in that the heterogeneous Ni-catalyst is Raney-Nickel.

3. The method according to claim 1, characterised in that the reducing agent used for the first reduction step is not a metal or mixed metal hydride reagent.

4. The method according to claim 1, characterised in that the reducing agent is selected from the group consisting of carbodiimides, Zn, formate, dithionite, Li, and mixtures thereof.

5. The method according to claim 1, characterised in that the catalytic hydrogenation is conducted at a hydrogen pressure of at least 5 bar.

6. The method according to claim 4, characterised in that the reducing agent is an alkali dithionite and/or zinc/ammonium formate.

7. The method according to claim 6, characterised in that molar ration of the Zn: ammonium formate couple is 1:1-5 ratio and wherein the molar ratio of Zn: educt of formula II is 1-1.5:1.

8. The method according to claim 1, characterised in that n=1 and R4 being para-C1-C4 alkyl or para-C1-C4 alkoxy, or n=0.

9. The method according to claim 1, characterised in that n=0.

10. The method according to claim 1, characterised in that R3 is a C1-C5-alkyl-thioether.

11. A method of synthesizing a compound of formula I,

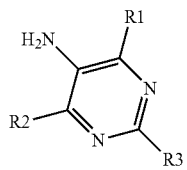

wherein R1, R2 are, independently, chloro or fluoro, and wherein R3 is H, aralkyl, alkyl or is an alkylether or alkylthioether, the alkyl moiety being linear or branched, comprising the step of catalytically hydrogenating the hydrazo compound of formula III

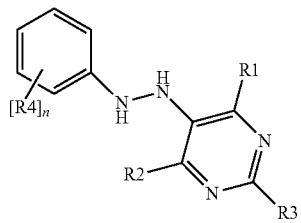

with a heterogeneous Ni-catalyst to the compound of formula I, wherein R1, R2, R3 are defined as above, n=0 to 5 and wherein $R4_n$ is halogeno alkyl or alkoxy.

12. The method according to claim 1 characterized in that R1, R2 are chloro.

13. The method according to claim 1, wherein the alkyl moiety or R3 is C1-C10 alkyl.

14. The method according to claim 1, wherein the alkyl moiety of R3 is C1-C4 alkyl.

15. The method according to claim 1, wherein the halogeno is chloro or fluoro.

16. The method according to claim 1, wherein the alkyl of $R4_n$ is C1-C6 alkyl and the alkoxy is C1-C6 alkoxy.

17. The method according to claim 1, wherein the reducing agent is selected from the group consisting of zinc-formate, zinc-copper salt couple or lithium-nickel salt couple, the latter in the presence of a catalytic amount of an arene.

18. The method according to claim 1, characterised in that the catalytic hydrogenation is conducted at a hydrogen pressure of from 8-12 bar.

19. The method according to claim 10, wherein the C1-C5-alkyl-thioether is selected from the group consisting of ethyl, n-propyl, isopropyl, tert, butyl, isobutyl or n-butyl.

20. The method according to claim 1, characterised in that R3 is a C1-C10 alkyl-thioether.

21. The method according to claim 11, wherein the alkyl moiety of R3 is C1-C10 alkyl.

22. The method according to claim 11, wherein the alkyl moiety of R3 is C1-C4 alkyl.

23. The method according to claim 11, wherein the heterogeneous Ni-catalyst is in the presence of gaseous $H_2$.

24. The method according to claim 11, wherein the halogeno is chloro or fluoro.

25. The method according to claim 11, wherein the alkyl of $R4_n$ is C1-C6 alkyl and the alkoxy is C1-C6 alkoxy.

26. The method according to claim 11, wherein $R4_n$ is H (n=0).

27. The method according to claim 11, wherein at least one $R4_n$ is halogeno.

28. The method according to claim 11, wherein $R4_n$ is chloro or fluoro.

29. The method according to claim 11, wherein $R4_n$ is C1-C6 alkyl or C1-C6 alkoxy.

* * * * *